United States Patent

Mosbach et al.

[11] Patent Number: 4,545,938
[45] Date of Patent: Oct. 8, 1985

[54] CHEMICAL SYNTHESIS

[75] Inventors: Erwin H. Mosbach; Misuho Une; Charles K. McSherry, all of New York, N.Y.

[73] Assignee: Beth Israel Medical Center, New York, N.Y.

[21] Appl. No.: 548,078

[22] Filed: Nov. 2, 1983

[51] Int. Cl.⁴ .............................................. C07J 9/00
[52] U.S. Cl. ................................................. 260/397.1
[58] Field of Search ..................................... 260/397.1

[56] References Cited

PUBLICATIONS

Fieser et al., (1959), "Steroids", Pub. Reinhold Publishing Corp., pp. 77,83,429.
Merck Index, (1976), Ninth Edition, pp. 2010 and 5392.

*Primary Examiner*—Elbert L. Roberts

[57] ABSTRACT

A compound of the formula,

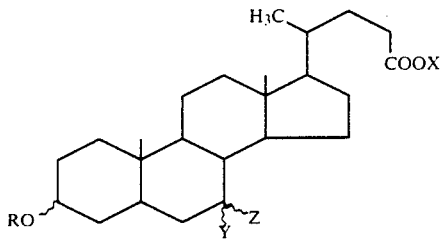

wherein R may be H or acyl; X may be H, acyl, or lower alkyl; Z may be H, hydroxy, or acyloxy; Y is lower alkyl; and the non-toxic pharmaceutically acceptable salts thereof.

This invention was made in the course of work performed under a grant from the United States National Heart Lung and Blood Institute.

10 Claims, No Drawings

CHEMICAL SYNTHESIS

This invention relates to and has as its objective the provision of novel compounds and new processes for their production. More particularly, this invention relates to the production of new physiologically active steroidal compounds and to novel processes for their production.

The final physiologically active compounds of this invention are compounds of the formula

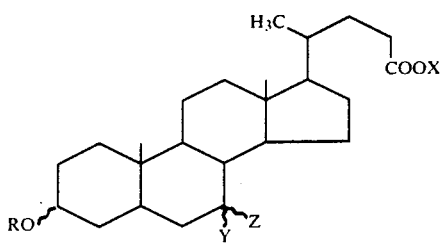

wherein R may be H or acyl; X may be H, acyl or lower alkyl; Z may be H, hydroxy or acyloxy; Y is lower alkyl; and the non-toxic, pharmaceutically acceptable salts thereof. In its most preferred embodiment, the practice of this invention provides compounds of the above formula, wherein R is H or acyl; X is H, acyl or methyl; Z is H, hydroxy or acyloxy; Y is methyl; and the non-toxic, pharmaceutically acceptable salts thereof, although the other final compounds of this invention also provide satisfactory results.

The final compounds of this invention are physiologically active compounds and may be employed in the therapeutic treatment of cholelithiasis disease in the same manner and to the same extent as disclosed for the 3,7-dihydroxy-cholanic acid derivatives in U.S. Pat. No. 3,859,437 issued Jan. 8, 1975. The amounts and periods of administration of the compounds of the instant invention to the patient being treated therewith is within the purview of the knowledge of the skilled worker and will depend on the condition of the patient being treated and the result desired.

In order to obtain the satisfactory results from the instant invention it will be necessary to administer the compounds of the instant invention to the patient being treated by a systemic route, for example, perorally, or parenterally. The compositions employed for such purposes should contain the compounds of this invention in a suitable systemically administerable, pharmaceutically acceptable composition, all as is well known to the skilled worker. Thus, suitable injectable compositions, orally administerable pills, capsules or elixirs or other suitable, pharmaceutically acceptable compositions containing the active compounds of this invention may be employed in the practice thereof. The skilled worker is well equipped to determine the most suitable compositions and dosage forms to be employed in the practice of the instant invention.

The acyl moieties which may be employed in the practice of this invention include those acyl groups which are derived from hydrocarbon carboxylic acids of twelve carbon atoms or less and include such acids as the alkanoic, cycloalkanoic, monocyclic acyl and monocyclic aralkyl acids.

Whenever in the specification hereof and the claims appended thereto in any structural formula contained therein a curved line ( $\}$ ) is employed in the linkage of atoms, it is meant to denote that the substituent moiety may be, stereochemically, in either the $\alpha$- or $\beta$-position, depending upon the compound involved.

The final compounds of this invention may be prepared in accordance with the processes of this invention employing as starting material the oxazoline derivative of a 3,7-dihydroxycholanic acid of the formula:

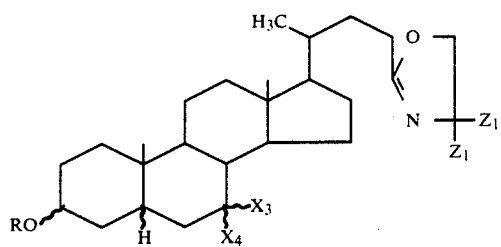

wherein R, $X_3$, $X_4$ and $Z_1$ are as defined in Column 1 of U.S. Pat. No. 4,371,528 issued Feb. 1, 1983. The foregoing starting materials may be prepared by the skilled worker in accordance with the teachings and disclosures of Ayengar, et al., steroids 38: pp 333–345 (1981) and those contained in U.S. Patent Application Ser. No. 294,338, filed Aug. 19, 1981.

The process of the instant invention may be illustrated by the following equations:

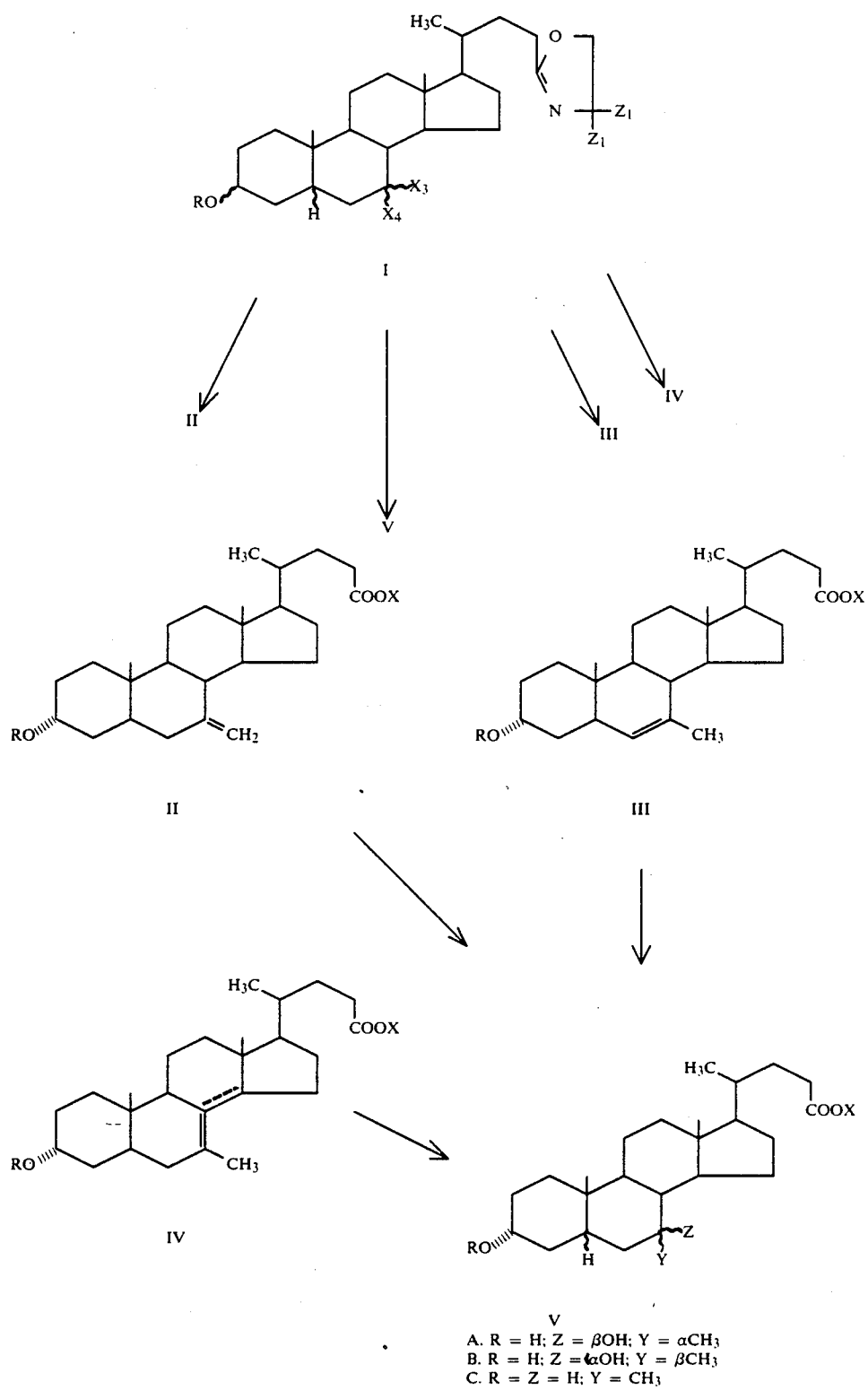

V
A. R = H; Z = βOH; Y = αCH₃
B. R = H; Z = αOH; Y = βCH₃
C. R = Z = H; Y = CH₃

In the first step of the process of this invention, the starting material, (Compounds I) is subjected to slow, mild hydrolysis, for example, by treatment with dilute mineral acid, such as, hydrochloric acid, at room temperature or slightly elevated temperature, around 37° C., over an extended period to yield the corresponding 7-hydroxy, 7-alkyl compounds (Compounds V) which are final compounds of this invention. Alternatively, the starting material (Compounds I) may first be treated with a methanolic mineral acid reactant to yield the dehydrated intermediate compounds (Compounds II, III and IV), which are novel compounds of this invention. These intermediates may then be hydrogenated, as by treatment with hydrogen in the presence of a platinum catalyst, to yield the final 7-alkyl compounds (Compounds V) of this invention.

The invention may be further illustrated by the following Examples.

EXAMPLE 1

3α,7β-Dihydroxy-7α-methyl-5β-cholanoic acid and 3α,7α-dihydroxy-7β-methyl-5β-cholanoic acid. Two grams of 2-(3α,7ξ-Dihydroxy-7ξ-methyl-24-nor-5β-cholanyl)-4,4-dimethyl-2-oxazoline was dissolved in a 0.1N HCl solution and incubated at 37° C. for 4 days. The solution was filtered and the precipitate obtained was dissolved in ethyl acetate. The ethyl acetate was washed with water until neutral and evaporated. The residue weighing 700 mg. was methylated with diazomethane and chromatographed on a silica gel column using a solvent system of increasing proportions of acetone in benzene. 12.5% acetone in benzene eluted the 7β-hydroxy isomer and 15% acetone yielded the 7α-hydroxy isomer. Alkaline hydrolysis of each isomer provided the free acids; 3α,7β-dihydroxy-7α-methyl-5β-cholanoic acid (150 mg; m.p. 102.5°–105° C.) and 3α,7α-dihydroxy-7β-methyl-5β-cholanoic acid (350 mg.; m.p. 95°–98° C.)

EXAMPLE 2

3α-Hydroxy-7ξ-methyl-5β-cholanoic acid. Ten grams of 2-(3α,7ξ-Dihydroxy-7ξmethyl-24-nor-5β-cholanyl)-4,4-dimethyl-2-oxazoline was refluxed with 200 ml. of 3N methanolic HCl and 1 ml. of water for 6 hours. The reaction mixture was poured into water and extracted with ether. Evaporation of the solvent left a mixture containing 6 grams of three unsaturated compounds. After being chromatographed on a silica gel column, impregnated with AgNO₃, using a solvent of increasing proportions of acetone in chloroform, the dehydration mixture separated into 3 separate fractions.

Hydrolysis of fraction 1 (1% acetone) with 5% methanolic KOH gave 2.1 grams of a mixture of 3α-hydroxy-7-methyl-5β-chol-7-enoic acid and 3α-hydroxy-7-methyl-5β-chol-8(14)-enoic acid.

Hydrolysis of fraction 2 (2% acetone), as above, gave: 3α-hydroxy-7-methyl-5β-chol-6-enoic acid (3.0 g, mp, 121°–122° C.). Hydrolysis of fraction 3, (2% acetone), as above, gave 3α-hydroxy-7-methylene-5β-cholanoic acid (1.1 g.; m.p. 104°–105° C.).

EXAMPLE 3

3α-Hydroxy-7ξ-methyl-5β-cholanic acid. The compounds obtained from fractions 2 and 3 from Example 2, above, were dissolved in ethyl acetate and reduced with hydrogen in the presence of a PtO₂ catalyst to yield a mixture of 3α-hydroxy-7α-methyl-5β-cholanic acid and 3α-hydroxy-7β-methyl-5β-cholanic acid.

The invention may be included within the scope of the appended claims.

What is claimed is:

1. A compound of the formula,

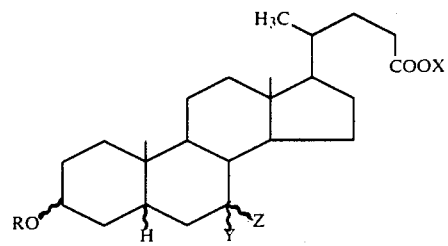

wherein R is H or acyl; X is H, acyl or alkyl; Z is H, hydroxy or acyloxy; Y is lower alkyl; and the non-toxic pharmaceutically acceptable salt thereof.

2. A compound of the formula,

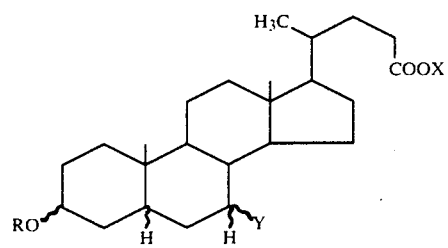

wherein R, Y and X are a defined in claim 1.

3. A compound of the formulae,

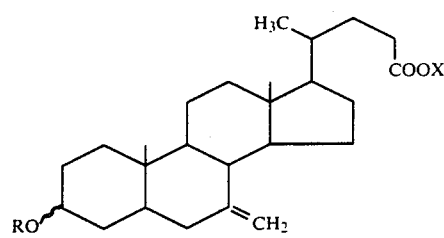

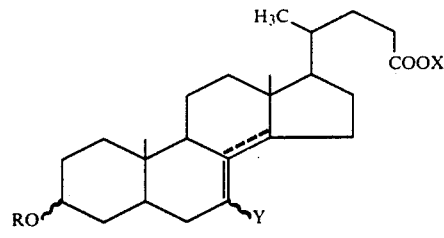

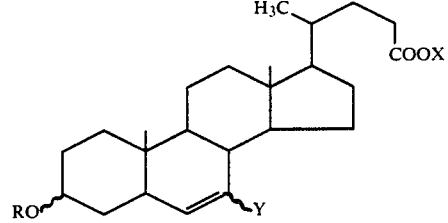

wherein R, X and Y are as defined in claim 1.

4. The compound of claim 1 wherein Y is methyl.

5. The compound of claim 1 wherein X is H.

6. The compound of claim 1 wherein R is H; X is H; Z is OH and Y is CH₃.

7. The compound of the formula,

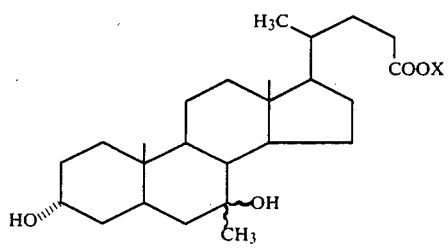
wherein X is as defined in claim 1.
8. A compound of claim 3 wherein X is H; R is H; and Y is CH₃.
9. 3α,7α-Dihydroxy-7β-methyl-5β-cholanoic acid.
10. 3α,7β-Dihydroxy-7α-methyl-5β-cholanoic acid.